(12) United States Patent
De Zanet et al.

(10) Patent No.: US 12,694,990 B2
(45) Date of Patent: Jul. 28, 2026

(54) PROGRESSION PROFILE PREDICTION

(71) Applicant: Ikerian AG, Bern (CH)

(72) Inventors: Sandro Ivo Sebastiano De Zanet, Bern (CH); Stefanos Apostolopoulos, Bern (CH); Carlos Ciller Ruiz, Bern (CH); Agata Justyna Mosinska-Domanska, Bern (CH)

(73) Assignee: Ikerian AG, Bern (CH)

( * ) Notice: Subject to any disclaimer, the term of this patent is extended or adjusted under 35 U.S.C. 154(b) by 315 days.

(21) Appl. No.: 18/556,106

(22) PCT Filed: Mar. 25, 2022

(86) PCT No.: PCT/EP2022/058001
§ 371 (c)(1),
(2) Date: Oct. 19, 2023

(87) PCT Pub. No.: WO2022/228794
PCT Pub. Date: Nov. 3, 2022

(65) Prior Publication Data
US 2024/0186022 A1 Jun. 6, 2024

(30) Foreign Application Priority Data
Apr. 20, 2021 (EP) ..................................... 21169441

(51) Int. Cl.
*G16H 50/50* (2018.01)
*G16H 10/60* (2018.01)
G16H 50/70 (2018.01)

(52) U.S. Cl.
CPC ............. *G16H 50/50* (2018.01); *G16H 10/60* (2018.01); *G16H 50/70* (2018.01)

(58) Field of Classification Search
CPC ........ G16H 50/50; G16H 10/60; G16H 50/70; G16H 50/20; G16H 50/30
(Continued)

(56) References Cited

U.S. PATENT DOCUMENTS

2018/0233233 A1* 8/2018 Sharma .................. G16H 50/30
2019/0223725 A1* 7/2019 Lu ........................... G06T 7/0012
(Continued)

FOREIGN PATENT DOCUMENTS

JP 2014514110 6/2014
JP 2019170706 A 10/2019

OTHER PUBLICATIONS

Alzubaidi Laith et al: " Review of deep learning: concepts, CNN architectures, challenges, applications, future directions", Journal of Big Data, Mar. 31, 2021 (Mar. 31, 2021), XP055955993, DOI: 10.1186/S40537-021-00444-8 Retrieved from the Internet: URL:https://journalofbigdata.springeropen.com/track/pdf/IO.1186/s40537-021-00444-8.pdf, [retrieved on Aug. 30, 2022] p. 9 penultimate par, p. 11 penultimate par.

(Continued)

*Primary Examiner* — Neil R McLean
(74) *Attorney, Agent, or Firm* — Ipsilon USA—NLO

(57) ABSTRACT

A method of predicting a progression of a condition comprises obtaining measurement data relating to at least one measurement on a subject up to a particular time point, wherein the data is generated based on an output of a sensor configured to perform the at least one measurement in respect of the subject. At least one parameter of a parameterized time-dependent function, wherein the parameterized time-dependent function is dependent on a continuous time value, is generated using a trained model and based on the measurement data, wherein the parameterized time-dependent function is indicative of a predicted progression of a condition of the subject over time after the particular time point. The parameterized time-dependent function is evaluated using the at least one parameter, for at least one time point after the particular time point.

15 Claims, 8 Drawing Sheets

401

(58) Field of Classification Search
USPC .......................................................... 382/128
See application file for complete search history.

(56)                    References Cited

U.S. PATENT DOCUMENTS

2022/0148290 A1*    5/2022    Zhang ................... G06V 10/764
2023/0237649 A1*    7/2023    Dillman ................. G16H 50/30
                                                                382/128

OTHER PUBLICATIONS

Apostolopoulos, S., De Zanet, S., Ciller, C., Wolf, S., Sznitman, R.: Pathological oct retinal layer segmentation using branch residual u-shape networks. In: Medical Image Computing and Computer Assisted Intervention. pp. 294-301 (2017).

Arcadu, F., Benmansour, F., Maunz, A., Willis, J., Haskova, Z., Prunotto, M.: Deep learning algorithm predicts diabetic retinopathy progression in individual patients. npj Digital Medicine 92(2) (2019).

Boyer, D.S., Schmidt-Erfurth, U., van Lookeren Campagne, M., Henry, E.C., Brittain, C.: The pathopysiology of geographic atrophy secondary to Age-related Macular Degeneration and the complement pathway as a therapeutic target. Retina 37(5) (2017).

Engwer, C., Hillen, T., Knappitsch, M., Surulescu, C.: Glioma follow white matter tracts: a multiscale dti-based model. Journal of mathematical biology 71 (Sep. 2014).

Fleckenstein, M., Mitchell, P., Freund, K.B., Sadda, S., Holz, F.G., Brittain, C., Henry, E.C., Ferrara, D.: The progression of geographic atrophy secondary to agerelated macular degeneration. Ophthalmology 125(3), 369{390 (2018).

Kingma, D.P., Ba, J.: Adam: A method for stochastic optimization. In: International Conference on Learning Representations (2015).

Mosayebi, P., Cobzas, D., Murtha, A., Jagersand, M.: Tumor invasion margin on the riemannian space of brain fibers. Medical Image Analysis 16(2), 361-373 (2012).

Niu, S., de Sisternes, L., Chen, Q., Rubin, D.L., Leng, T.: Fully automated prediction of geographic atrophy growth using quantitative Spectral-Domain Optical Coherence Tomography biomarkers. Ophthalmology 123(8), 1737{1750 (2016).

Petersen, J., Jager, P.F., Isensee, F., Kohl, S.A.A., Neuberger, U., Wick, W., Debus, J., Heiland, S., Bendszus, M., Kickingereder, P., Maier-Hein, K.H.: Deep Probabilistic Modeling of Glioma Growth (2019).

Ronneberger, O., Fischer, P., Brox, T.: U-net: Convolutional networks for biomedical image segmentation. In: Medical Image Computing and Computer-Assisted Intervention. vol. 9351, pp. 234{241 (2015).

Sadda, S.R., Guymer, R., Holz, F.G., Schmitz-Valckenberg, S., Curcio, C.A., Bird, A.C., Blodi, B.A., Bottoni, F., Chakravarthy, U., Chew, E.Y., Csaky, K., Danis, R.P., Fleckenstein, M., Freund, K.B., Grunwald, J., Hoyng, C.B., Jaffe, G.J., Liakopoulos, S., Monés, J.M., Pauleikhoff, D., Rosenfeld, P.J., Sarraf, D., Spaide, R.F., Tadayoni, R., Tufail, A., Wolf, S., Staurenghi, G.: Consensus definition for atrophy associated with Age-Related Macular Degeneration on OCT: classification of atrophy report 3. Ophthalmology 125(4), 537-548 (2018).

Zhang, Y., Ji, Z., Niu, S., Leng, T., Rubin, D.L., Chen, Q.: A multi-scale deep convolutional neural network for joint segmentation and prediction of geographic atrophy in SD-OCT images. 2019 IEEE 16th International Symposium on Biomedical Imaging ISBI 2019) (ISBI), 565-568 (2019).

Niu, S., de Sisternes, L., Chen, Q., Leng, T., Rubin, D.L.: Automated geographic atrophy segmentation for SD-OCT images using region-based C-V model via local similarity factor. Biomedical Optics Express 7(2), 581 (2016).

* cited by examiner

301
Input

303
Processor

302
Storage (a)        (b)        (c)        (d)

PROGRESSION PROFILE PREDICTION

FIELD OF THE INVENTION

The invention relates to predicting a progression profile. The invention further relates to training a model to predict a progression profile.

BACKGROUND OF THE INVENTION

In medical imaging, for example, one may assess a condition of a subject based on, for example, a medical image and/or other measurements, such as temperature and heart rate. Also, attempts have been made to predict a future condition of a patient based on a medical image.

Zhang et al.: 'A multi-scale deep convolutional neural network for joint segmentation and prediction of geographic atrophy in SD-OCT images', 2019 IEEE 16th International Symposium on Biomedical Imaging (ISBI 2019) pp. 565-568 discloses to train a model to jointly segment GA and predict a future time point segmentation using a deep neural network.

SUMMARY OF THE INVENTION

It is an object of the invention to be able to provide an improved prediction of a progression profile.

According to an aspect of the invention, a method of predicting a progression of a condition is provided. The method comprises:

obtaining measurement data relating to at least one measurement on a subject up to a particular time point, wherein the data is generated based on an output of a sensor configured to perform the at least one measurement in respect of the subject;

generating at least one parameter of a parameterized time-dependent function, using a trained model and based on the measurement data, wherein the parameterized time-dependent function is indicative of a predicted progression of a condition of the subject over time after the particular time point.

The method may further comprise evaluating the parameterized time-dependent function using the at least one parameter, for at least one time point after the particular time point.

According to another aspect of the invention, a method of training a model to predict a progression of a condition is provided. The method comprises:

obtaining training data comprising measurement data relating to at least one measurement on at least one subject, wherein the measurement data is based on an output of a sensor configured to perform the at least one measurement in respect of the subject, the training data further comprising, for each subject, at least one time point associated with the subject, and information indicative of a condition of the subject at the at least one time point;

generating at least one parameter of a parameterized time-dependent function, using a model and based on the measurement data of a certain subject of the at least one subject, wherein the parameterized time-dependent function is indicative of a predicted progression of the condition of the certain subject over time;

evaluating the parameterized time-dependent function using the at least one parameter, for the at least one time point associated with the certain subject, to obtain a predicted condition of the subject at the at least one time point;

comparing the predicted condition of the certain subject at the at least one time point associated with the certain subject to the information in the training data indicative of the condition of the certain subject at the at least one time point associated with the certain subject, to obtain a comparison result; and updating the model based on the comparison result.

In certain embodiments, at least one first subject of the at least one subject has a first set of at least one time point associated therewith, at least one second subject of the at least one subject has a second set of at least one time point associated therewith, and at least one time point in the first set is different from each time point in the second set.

The at least one parameter may be indicative of a time point when the condition will change or a speed at which the condition will change.

The step of evaluating the parameterized time-dependent function may comprise applying a threshold to the parameter that is generated using the model, wherein the threshold depends on the time point at which the parameterized time-dependent function is evaluated.

The at least one parameter may comprise at least one coefficient of a term of the parameterized time-dependent function.

The parameterized time-dependent function may comprise a Fourier series or a Taylor series.

The measurement data may comprise at least one N-dimensional input dataset associated with the subject, generated by a data capturing device. Herein, N is an integer value greater than or equal to 1. Preferably, N is an integer value greater than or equal to 2.

In a particular example, the N-dimensional input dataset is an at least two-dimensional image dataset and the data capturing device is an imaging device.

The step of generating at least one parameter may comprise generating the at least one parameter for each of a plurality of locations corresponding to locations within the N-dimensional input dataset, to define the parameterized time-dependent function for each of the plurality of locations separately.

The measurement data may comprise at least one at least two-dimensional image dataset associated with the subject, generated by an imaging device.

The step of generating at least one parameter may comprise generating the at least one parameter for each of a plurality of locations corresponding to locations within the at least two-dimensional image dataset, to define the parameterized time-dependent function for each of the plurality of locations separately.

The model may comprise a convolutional neural network.

According to another aspect of the invention, an apparatus is provided for predicting a progression of a condition. The apparatus comprises:

an input configured to receive measurement data relating to at least one measurement on a subject up to a particular time point, wherein the data is generated based on an output of a sensor configured to perform the at least one measurement in respect of the subject;

a non-transitory storage media comprising a model; and a processor system configured to cause the apparatus to generate at least one parameter of a parameterized time-dependent function, using the model and based on the measurement data, wherein the parameterized time-dependent function is indicative of a predicted progression of a condition of the subject over time after the particular time point.

According to another aspect of the invention, an apparatus is provided for training a model to predict a progression of a condition. The apparatus comprises:

an input configured to receive training data comprising measurement data relating to at least one measurement on at least one subject, wherein the measurement data is based on an output of a sensor configured to perform the at least one measurement in respect of the subject, the training data further comprising, for each subject, at least one time point associated with the subject, and information indicative of a condition of the subject at the at least one time point;

a storage media for storing a model; and a processor system configured to cause the apparatus to:

generate at least one parameter of a parameterized time-dependent function, using the model and based on the measurement data of a certain subject of the at least one subject, wherein the parameterized time-dependent function is indicative of a predicted progression of the condition of the certain subject over time, evaluate the parameterized time-dependent function using the at least one parameter, for the at least one time point associated with the certain subject, to obtain a predicted condition of the subject at the at least one time point, compare the predicted condition of the certain subject at the at least one time point associated with the certain subject to the information in the training data indicative of the condition of the certain subject at the at least one time point associated with the certain subject, to obtain a comparison result, and update the model based on the comparison result.

By using a parameterized time-dependent function as the basis for predicting the progression profile of the condition, the prediction is not tied to a specific time point, but can instead be evaluated at any time point, in particular any time point in the future or after the last available measurement. This enables comparing the prediction to the reality at any time for which new diagnostic data is available. This provides flexibility in planning. For example, it may provide flexibility in treatment planning, including but not limited to adherence monitoring and monitoring the response to treatment.

When training the model, the parameterized time-dependent function makes it possible to handle ground truth data that may be available at non-periodic or irregular time intervals for the different subjects.

The simple example for a time-dependent function may be a step function. The threshold technique may be advantageous in particular for a monotonically progressive disease, where the parameter generated using the model may be indicative of the speed at which the condition changes. This provides a particularly small number of parameters to be estimated by the model (for example, just one parameter).

A more complex parameterized function, such as a finite Fourier or Taylor series, may be useful to predict the progression profile in greater detail, allowing to encode relatively complex time-dependent behavior in an efficient way. This may allow the model to be trained more efficiently.

The person skilled in the art will understand that the features described above may be combined in any way deemed useful. Moreover, modifications and variations described in respect of the system may likewise be applied to the method and to the computer program product, and modifications and variations described in respect of the method may likewise be applied to the system and to the computer program product.

BRIEF DESCRIPTION OF THE DRAWINGS

In the following, aspects of the invention will be elucidated by means of examples, with reference to the drawings. The drawings are diagrammatic and may not be drawn to scale. Throughout the drawings, similar items may be marked with the same reference numerals.

FIG. 3 shows a block diagram illustrating an apparatus for predicting a condition or training a model.

FIG. 7A shows Dice scores of evaluated methods.

FIG. 7B shows Area Difference scores of evaluated methods.

DETAILED DESCRIPTION OF EMBODIMENTS

Figure 1:
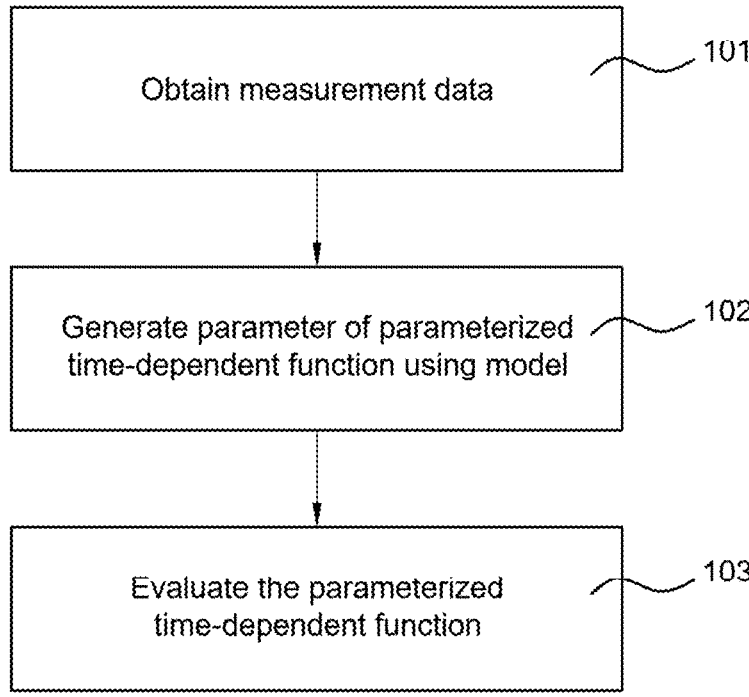
FIG. 1 shows a flowchart illustrating a method of predicting a progression of a condition.

Certain exemplary embodiments will be described herein in greater detail, with reference to the accompanying drawings.

The matters disclosed in the description, such as detailed construction and elements, are provided to assist in a comprehensive understanding of the exemplary embodiments. Accordingly, it is apparent that the exemplary embodiments can be carried out without those specifically defined matters. Also, well-known operations or structures are not described in detail, since they would obscure the description with unnecessary detail.

In the following, certain aspects are disclosed in relation to the example of geographic atrophy of the visual system, which may be diagnosed on the basis of 3-d depiction of retinal structures by optical coherence tomography. However, it should be understood that in general the technique can be applied to any disease or condition, and any other imaging modality such as computed tomography, magnetic resonance imaging, echography, and any other imaging equipment may be used instead, depending mainly on the disease or condition to be assessed. Also, the technique may be applied to two-dimensional images, such as photographs and X-ray images, and one-dimensional data, such as blood pressure or temperature. Moreover, multiple measurements of the same type or different types may be combined and assessed together. Moreover, measurements may be preprocessed, so that the model is trained with preprocessed data rather than the raw data. For example, in case of geographic atrophy, the optical coherence tomography dataset may be converted into a number of layer thicknesses.

It will be understood that the techniques disclosed herein may be applied to N-dimensional input datasets, such as N-dimensional images, wherein N may be 1, 2, 3, or any positive integer value. An example of suitable 3-dimensional image datasets is MRI volume scans.

In many diseases, the disease influences the condition of a certain region of the body. This can be detected using one of many available imaging techniques. The area of growth of the disease may not be uniform. When the disease progresses, the area of growth of the disease may increase. However, the shape of the diseased area can also change over time and it may be difficult to predict which anatomical region(s) will be affected by the disease and when. The techniques disclosed herein may help to address these concerns.

The known training techniques are based on curated data, where consecutive acquisitions are taken at specific time points, e.g. at regular intervals that are identical for each patient. This is however not realistic for most clinical applications, as patients may have different frequencies of acquisitions and possibly interruptions in the visits. Moreover, the inference results may not be reliable if we are interested in predicting different time intervals beyond the time point(s) for which the model was trained. The techniques disclosed herein may allow for much more flexible training and prediction, as it does not assume that acquisitions are taken at uniform time points. Instead, we predict a general growth pattern using a parametric function to encode the course of the disease over time. This allows to extrapolate what may be the final condition of the patient's visual system and, for example, design a treatment plan.

In our method we loosen the constraint of predicting future time points at specific intervals and instead build a single continuous model of predicted progression of the condition. Although the detailed description discloses the example of geographic atrophy, the techniques disclosed herein are not limited thereto. This single continuous model may be provided in the form of level sets, for example. More generally, the single continuous model may be provided in the form of the parameters of a parametric time-dependent function. This way, only a few parameters are necessary to denote a potentially relatively complex progression profile.

For example, the available input data may be incorporated in a single input tuple I, which may be a matrix or a tensor, for example. The set of at least one parameter to be estimated may be represented by output prediction G, which may be a vector or a matrix. The model to be trained represents a mapping $f_\theta$ that maps the input tuple I to the output prediction G. The mapping $f_\theta$ may be implemented as a neural network, for example. An example neural network is a convolutional neural network. Instead of a neural network, a statistical model could be used, such as a linear regression model or a non-linear regression model. The symbol $\theta$ represents the model parameters, e.g. the configuration of the neurons of a neural network, which can be updated during the training procedure.

In certain embodiments, for example in case of a monotonously progressing disease or condition, the output prediction G may be represented by a single numeric value. The consequence is that G may predict all future growth of an affected area, for example a GA area. By finding a threshold $T_i$ for a corresponding time point $t_i$, we can find the affected area's extent by testing whether the value of G is greater than the threshold $T_i$. This makes our approach much more flexible as compared to the existing techniques, which are trained to predict atrophy only at a specified time interval (e.g. 6 or 12 months after the last measurement). Thanks to predicting the progression profile, we can define the progression of the affected area at any given future time point.

In case of a regional condition, such as GA, the output prediction G may include the single numeric value for every pixel (or voxel) for which the prediction is desired. For each time point $t_i$ and each corresponding value of the threshold $T_i$, a separate image may be generated by setting the pixels/voxels for which $G>T_i$ to a different value or color than the pixels/voxels for which $G\leq T_i$.

In certain embodiments, the output prediction G may comprise at least one parameter of a parametric function. An example of a suitable parametric function is a Taylor sequence with N terms:

$$g(x) = \sum_{n=0}^{N-1} a_n(x-b)^n.$$

Herein, the parameters are $a_n$ (for all integers n from 0 to and including N−1) and b. This results in a total of N+1 parameters. The model may thus be trained to output the parameters $a_n$ (for all integers n from 0 to and including N−1) and b, when the input tuple I is applied to the model. In certain embodiments, the value b may be predefined beforehand. For example, b may be fixed to a specific value, such as zero, in particular when the data is normalized so that time point 0 is set to coincide with the data acquisition, for example. In such a case, the model needs only predict the N parameters $a_n$ (for all integers n from 0 to and including N−1). So, for example, the model should output a tuple ($a_0$, $a_1$, $a_2$, . . . , $a_{N-1}$). For example, N may be an integer in the range from 1 to 20, preferably in the range from 2 to 20, more preferably in the range from 2 to 10, even more preferably in the range from 2 to 5.

Another example of a parametric function is a Fourier series with 2N+1 terms, determined for a period P:

$$g(x) = \frac{a_0}{2} + \sum_{n=1}^{N}\left(a_n \cos\left(\frac{2\pi nx}{P}\right) + b_n \sin\left(\frac{2\pi nx}{P}\right)\right).$$

Here, the parameters are $a_n$ (for all integers n from 0 to and including N) and $b_n$ (for all integers n from 1 to and including N). Thus, in this case, for example, the model should output a tuple ($a_0$, $a_1$, $a_2$, . . . , $a_N$; $b_1$, $b_2$, . . . , $b_N$). Again, for example, N may be an integer in the range from 1 to 20, preferably in the range from 2 to 20, more preferably in the range from 2 to 10, even more preferably in the range from 2 to 5.

Yet another example of a parametric function is a Fourier series expressed in the amplitude-phase form, with 2N+1 terms:

$$g(x) = \frac{A_0}{2} + \sum_{n=1}^{N} A_n \cos\left(\frac{2\pi nx}{P} - \varphi_n\right).$$

Here, the parameters are $A_n$ (for all integers n from 0 to and including N) and $\varphi_n$ (for all integers n from 1 to and including N). Thus, in this case, for example, the model should output a tuple ($A_0$, $A_1$, $A_2$, . . . , $A_N$; $\varphi_1$, $\varphi_2$, . . . , $\varphi_N$). Again, for example, N may be an integer in the range from 1 to 20, preferably in the range from 2 to 20, more preferably in the range from 2 to 10, even more preferably in the range from 2 to 5.

The choice of the parametric time-dependent function may be chosen in view of the typical progression of the condition that is being predicted in a larger population.

In certain embodiments, the model (neural network, statistical model) may be trained on processed data. That is, the inputs of the model may be not raw sensor data, but preprocessed data such as segmented data or normalized data, for example. Moreover, the outputs may not be the actual parameters of the parameterized function, but may be subjected to post-processing operations, such as normalization, for example, to account for different time spans or different amplitudes.

Although the examples in the disclosure emphasize the medical application domain, it will be understood that the present techniques may also be applied to other time-evolving applications, such as machine component failure, non-destructive testing, non-medical imaging, or weather forecasting. Use may be made of X-ray, photography, radar, or other sensor techniques to obtain the measurement data, for example. The condition to be predicted may comprise, for example, a predicted time of component failure or predicted efficiency of a machine or component as a function of time. The term subject used herein may refer to, for example, an object or a patient.

FIG. 1 shows a method of predicting a progression of a condition. In certain embodiments, the method may be a computer-implemented method. In step 101, measurement data is obtained relating to at least one measurement on a subject. The measurement data may be obtained, for example, from an imaging modality. The measurement data may relate to a measurement at one time, or to measurements made at a plurality of different times. The most recent measurement was performed at a particular time point. The data is generated based on an output of a sensor configured to perform at least one measurement in respect of the subject. For example, an output signal of the sensor is sampled and processed to obtain sensible measurement data. For example, optical sensor data is combined to form a three-dimensional volume using optical coherence tomography. Further, the data may be processed in a way to aid the prediction of the condition. In case of geographic atrophy, this may involve identifying several layer thicknesses. In case of other applications, this may involve a suitable preprocessing, such as, but not limited to, segmentation, noise reduction, edge enhancement, normalization, and the like.

In step 102, the measurement data is used to generate at least one parameter of a parameterized time-dependent function. To that end, the measurement data may be further preprocessed into suitable inputs of a model, which may be a neural network in certain embodiments. This optional preprocessing may be application specific and further details thereof are omitted in the present disclosure. The inputs of the model are determined based on the measurement data and fed to the model. The model is configured to generate an output in response to the input. And the output of the model may comprise at least one parameter of a parametric time-dependent function. Optionally, the output of the model is processed to obtain the at least one parameter. For example, a normalization of the output of the model may be performed. Other such optional post-processing operations may include, but are not limited to, scaling operations and combination operations in which multiple outputs of the model are combined into one parameter.

For example, the parameterized time-dependent function is dependent on a continuous time value.

In step 103, the parameterized time-dependent function may be evaluated at any desired time point for which the parameterized time-dependent function is valid. This way, the future condition may be predicted. Evaluation may comprise, in certain embodiments, comparing the parameter to a time-dependent threshold. Each time-dependent threshold can be used to create a segmentation of the parameter. Thus, a segmentation can be generated for any desired time point.

In certain embodiments, evaluation of the parameterized time-dependent function at a given time point t may involve filling in the at least one parameter and the time point t in a formula (which may be based on e.g. a Taylor or Fourier series) and calculate the result.

In certain embodiments, the parameter is generated using the model for each of a plurality of picture elements (e.g. pixels or voxels) of an image dataset. The value of each picture element may be evaluated using the parameterized time-dependent function for any time value t. Thus, for each time t, an image can be generated using the values of each picture element.

In certain embodiments, the parameterized time-dependent function may have multiple arguments. In such a case the function g may be written as g(t, x), for example. Herein, g denotes the parameterized time-dependent function, which depends on the time t and at least one other argument x. Thus, the parameterized time-dependent function may depend on time and at least one further argument. As an example, the parameterized time-dependent function may be further dependent on the amount of time until the next treatment, in months. Varying the time of treatment then changes the outcome of the parameterized time-dependent function. If the disease is treated early, the growth of the disease may be smaller or slower, whereas if the disease is treated later, the treatment may be less effective, with the consequence of larger or quicker growth of the disease. This means that the time-dependent function can also depend on at least one further argument, besides the time for which the prediction is made. An example of such a further argument is the time at which a certain event, such as a treatment, will take place.

Figure 2:
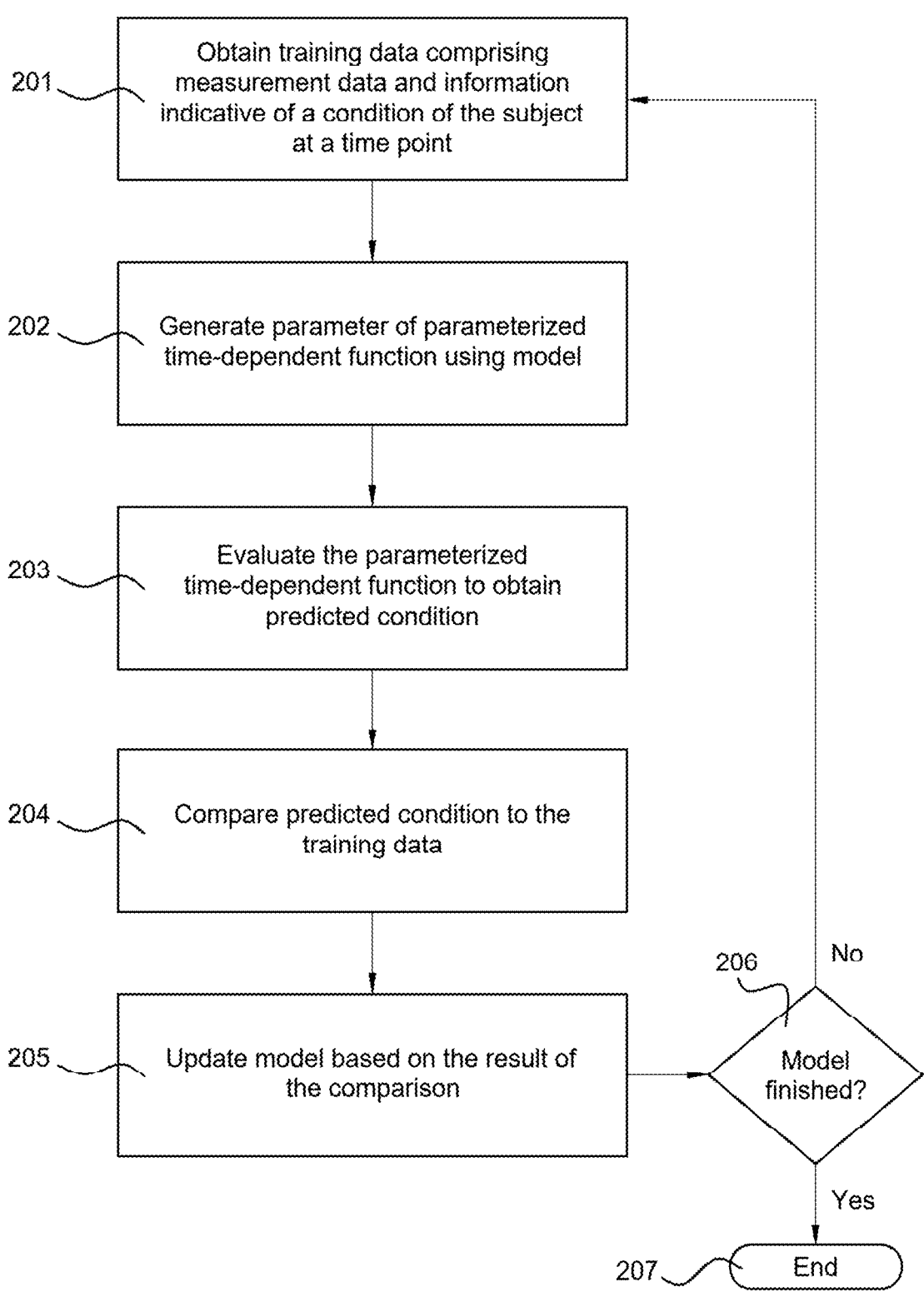
FIG. 2 shows a flowchart illustrating a method of training a model to predict a progression of a condition.

FIG. 2 illustrates a method of training the model to predict a progression of a condition. For example, the method may start with an initial model. The initial model may be set using random model parameters or be based on prior knowledge, for example. The model may comprise a neural network or a statistical model, for example.

In step 201, training data is obtained. The training data may comprise measurement data relating to at least one measurement on at least one subject. For example, one measurement may be provided for each of a plurality of subjects. Alternatively, a set of measurements, performed over time, may be provided in respect of each of a plurality of subjects. In certain embodiments, the number of measurements may be different for each subject. The measurements may be similar to the measurement data used in the method of FIG. 1.

The measurement data is based on an output of a sensor configured to perform at least one measurement in respect of the subject. For example, the data may be generated by an imaging device used to image a part of a patient.

The training data may comprise, for each subject, at least one time point associated with the subject, and information indicative of a condition of the subject at the at least one time point. This information may be used as ground truth data. The model is trained in this method to output similar information in response to the measurement data of a subject. On that basis, training data may be generated in form of inputs and outputs showing the desired behavior of the model.

In certain embodiments, the information indicative of a condition of the subject at the at least one time point is determined based on a further measurement performed in respect of the subject at that time point. For example, if measurement data is available for a first time point and a second, later, time point, the measurement data for the second time point may be used to determine the information indicative of the condition of the subject at the second time point (to be predicted by the model).

In certain embodiments, the information indicative of the condition of the subject at the second time point is automatically extracted from the measurement data at the second time point, for example using a computerized algorithm. In other embodiments, the information indicative of the condition of the subject at the second time point is manually created based on the measurement data at the second time point, by a human specialist. In yet other embodiments, the measurement data itself may be the condition to be predicted.

In certain embodiments, training pairs are generated, each training pair comprising measurement data relating to a subject for a first time point and information about the condition of the subject at a second time point, the second time point being later in time than the first time point. The measurement data for the first time point may be used to generate the inputs of the model, and the information about the condition at the second time point may be used to assess the model's performance so as to improve the model.

In step 202, at least one parameter of a parameterized time-dependent function is generated, using the model and based on the measurement data of a certain subject of the at least one subject. As described above, the measurement data may be preprocessed to obtain the corresponding inputs of the model. The parameterized time-dependent function is indicative of a predicted progression of the condition of the certain subject over time.

In step 203, the parameterized time-dependent function is evaluated using the at least one parameter, for the at least one time point associated with the certain subject, to obtain a predicted condition of the subject at the at least one time point. This step provides data that is suitable to be compared to the ground truth condition of the subject stored in the training data.

In step 204, the predicted condition of the certain subject at the at least one time point associated with the certain subject is compared to the information in the training data indicative of the condition of the certain subject at the at least one time point associated with the certain subject. This comparison step may result in a comparison result, such as an error measure or a goodness of fit.

One of the advantages of the techniques disclosed herein, is the possibility to make use of uncurated data, in the sense that the intervals between the times for which the ground truth information about the condition is made available, does not have to be the same for all the subjects. For example, a first subject can have a first set of time points associated therewith and information indicative of the condition of the subject at each time point of the first set of time points. A second subject can have a second set of time points associated therewith and information indicative of the condition of the subject at each time point of the second set of time points. In uncurated data, it is possible that at least one time point in the first set is not present in the second set. Moreover, it is even possible that a time point associated with a first subject is not associated with any of the other subjects. The ground truth information for any time point can be compared to the model output by evaluating the parametric time-dependent function at that time point.

In step 205, the model is updated based on the comparison result. In certain embodiments, the comparison result of a plurality of subjects is combined in a combined comparison result, and the model is updated based on the combined comparison result.

After the model has been updated, it is determined in step 206 if the training is complete. If the training is not yet complete, the process is restarted from step 201, using the updated model as the current model. If it is determined at step 206 that the model is finished, the process ends in step 207. The process of FIG. 1 may thereafter be performed using the final model of the method of FIG. 2.

Figure 3:
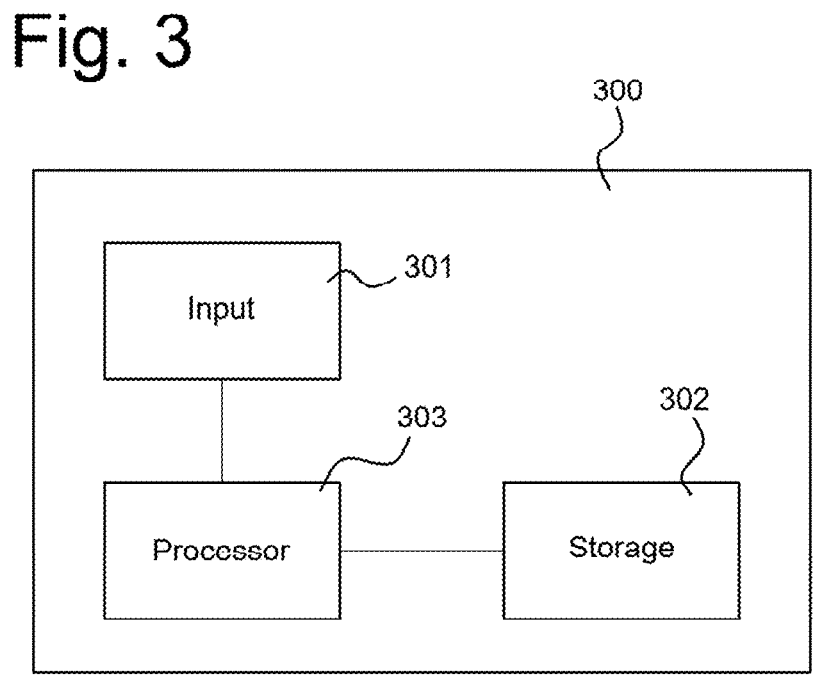

FIG. 3 shows an apparatus 300 for predicting a progression of a condition. In certain embodiments, the apparatus 300 may be also configured for training the model to predict a progression of a condition. The apparatus 300 comprises an input 301. The input 301 may comprise a communications port, such as a network interface or data bus, for receiving data. The apparatus 300 may further comprise a storage media 302. Storage media 302 may comprise a computer memory. Storage media 302 may also comprise non transitory computer readable media with computer instructions stored thereon. When executed by the processor 303, the apparatus may be configured to carry out the steps of any of the methods set forth herein. The storage media 302 may also store a model, such as a neural network model. The storage media 302 may also store measurement data and/or training data. The processor system 303 may control the apparatus 300 by executing the instructions in the storage 302. It will be understood that the details of the training procedure may be implemented differently, although the at least one parameter is generated based on the output of the model and the model is updated based on the result of evaluating the parameterized time-dependent function at a certain time point for which ground truth data is available.

In the following, certain embodiments will be disclosed in greater detail. It will be understood that the description of these detailed embodiments serves to illustrate, rather than to limit, the scope of protection.

Geographic Atrophy (GA) is a disease affecting the visual system, characterized by the loss of photoreceptor cells in the retina. Depending on the location, GA may have different functional consequences: When the central (foveal) part of the retina is affected, visual acuity is compromised to a higher degree than if peripheral regions are damaged. For that reason it is crucial to be able to predict in which direction the disease may propagate and to predict its spread rate. Current approaches to prediction of GA progression tackle only the next (arbitrarily chosen or visit-imposed) time point necessitating highly curated data at fixed points in time. Due to the nature of patient visits, this kind of data is often hard to acquire in a real-world clinical setup, even when patients are following a treatment protocol. These scenarios hinder the development of new disease progression strategies. We present a novel approach to predicting a continuous GA growth based on layer thickness of a single scan. The method is framed as a level set problem, which models the complete progression pattern of GA in the patient and does not require uniform acquisition intervals.

1. Introduction

GA, a degenerative disease of the retina, is an advanced form of Age-Related Macular Degeneration (AMD) that causes irreversible damage to the Photoreceptors (PR). This in turn causes loss of vision and manifests itself as dark patches in a patient's visual field. Depending on the location in the retina, GA may have different effects on vision. It is a chronic disease with no cure, thus, physicians focus on slowing down the disease. Progression mechanisms are not clearly understood and there is ongoing research in this direction [5]. Automated detection and progression prediction algorithms can reduce the workload involved in analyzing images and give insights into contributing factors. Existing approaches to GA progression are based mainly on Optical Coherence Tomography (OCT), which allows for 3-d depiction of retinal structures at high resolution. Niu et al. [9] present a method to predict GA growth probability based on various retinal layer thicknesses and projection images using Random Forests (RF). Using a time-weighted threshold, they predict the GA region at a future time point. Zhang et al. train a model to jointly segment GA and predict a future time point segmentation using a deep neural network. Arcadu et al. [2] predict Diabetic Retinopathy progression by means of Deep Learning (DL) applied on color fundus photographs.

Prediction of disease progression has been also performed in various fields other than ophthalmology at different levels of granularity. Brain tumour growth has been probabilistically modelled using biological models [4, 7] or more recently using deep probabilistic modelling [10]. There, Petersen et al. propose a learned distribution of plausible growth trajectories, with the assumption that tumour growth behaves differently from patient to patient. All the above methods are trained using curated data, where consecutive acquisitions are taken at specific time points. This is however not realistic for most clinical applications, as patients may have different frequencies of acquisitions and possibly interruptions in the visits. Moreover, the inference results may not be reliable if we are interested in predicting different time intervals beyond the original time point for which the model was trained. In contrast, we present a method that allows for much more flexible training and prediction, as it does not require acquisitions to be taken at uniform time points. Instead, we predict a general growth pattern, which shows regions of the retina that are most prone to progression. By thresholding the predicted disease profile, we obtain GA prediction at future time points. This allows clinicians to extrapolate what may be the final condition of the patient's visual system and design the treatment plan.

2. Method

Given a 3-d OCT volume $X_{t_0}$ of size D×H×W acquired at time $t_0$ our goal is, for example, to predict current GA and its future time steps at time $t > t_0$. These predictions are created on the en-face projection (along the depth axis D) of the volumetric data, which corresponds to the area seen with fundus imaging. In our method we loosen the constraint of predicting future time points at specific intervals and instead build a single continuous model of atrophy growth in the form of level sets.

Previous literature showed that retinal layer information is particularly important for atrophy detection [8, 13]. We therefore first perform layer and fluid segmentation using the algorithm of [1]. An example output is shown in FIG. 4B. GA is the depletion of PR cells, however, neighboring retinal layers are also affected by this cell death. Hence, we compute the 2-d en-face thickness measurements corresponding to each segmented layer (as illustrated in FIG. 5):

Retinal Nerve Fibre Layer (RNFL),
Ganglion Cell Layer (GCL) and Inner Plexiform Layer (IPL)
Inner Nuclear Layer (INL) and Outer Plexiform Layer (OPL)
Outer Nuclear Layer (ONL)
Photoreceptors (PR) and Retinal Pigment Epithelium (RPE)
Choriocapillaris (CC) and Choroidal Stroma (CS) and similarly the thickness of 3 fluid types:
Intraretinal Fluid (IRF)
Subretinal Fluid (SRF)
Pigment Epithelium Detachment (PED).

Figure 5:
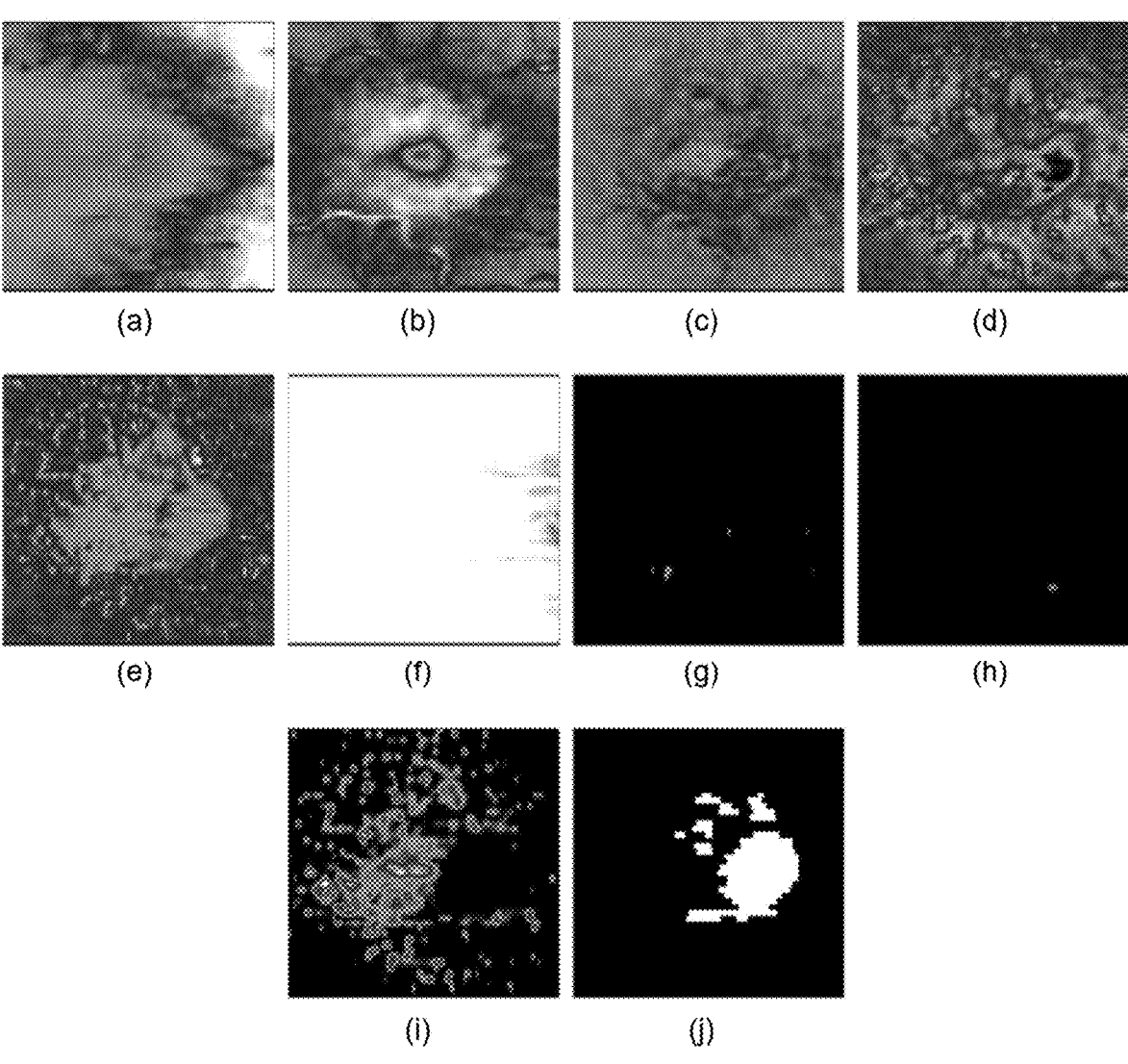
FIG. 5A to I show an example of input thickness maps for a network of projected volume segmentations.
FIG. 5J shows a manual segmentation of atrophy.

FIG. 5 shows an example of input thickness maps for the network. In this regard, FIG. 5A shows RNFL, FIG. 5B shows GCL+IPL, FIG. 5C shows INL+OPL, FIG. 5D shows ONL, FIG. 5E shows PR+RPE, FIG. 5F shows CC+CS, FIG. 5G shows IRF, FIG. 5H shows SRF, FIG. 5I shows PED, and FIG. 5J shows the manual segmentation of atrophy. These figures correspond to en-face projections of OCT volume.

We combine all thickness maps into a single input tensor $I_{t_0} \in \mathbb{R}^{C \times H \times W}$. Our goal is then to find a mapping $f_\theta$:

$$f_\theta: I_{t_0} \to G_{t > t_0} I_{t_0} \in \mathbb{R}^{C \times H \times W}, G_{t > t_0} \in \mathbb{R}^{H \times W}$$

where $G_{t > t_0}$ is a single-channel output prediction of the same size as the thickness maps.

The higher the value of a given pixel in the map, the bigger the probability that the corresponding area is/will develop GA. By looking at the level sets of $G_{t > t_0}$ we find the full future progression of the disease. Note that this formulation only works under the assumption that a region already affected by GA does not heal back (or regrow), i.e. we can assume GA growth to be monotonous. Since, to our knowledge, there is no therapy to regrow PR cells, the assumption holds true in this case.

The consequence is that $G_{t > t_0}$ predicts all future growth of the GA area. By finding a threshold $T_i$ for a corresponding time point $t_i$, we can find the GA extent by computing $G_i = G_{t > t_0} > T_i$. This makes our approach much more flexible as compared to the existing techniques, which are trained to predict atrophy only after a specified time (e.g. 6 or 12 months). Thanks to predicting the progression profile, we can define the GA progression at any given future time point.

2.1. Training

Figure 4A:
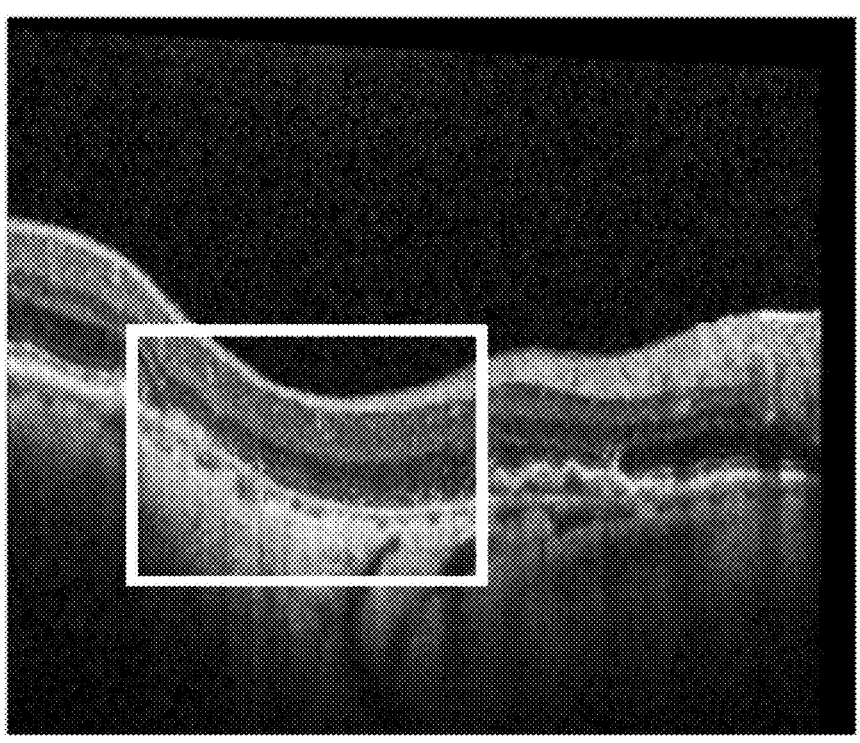
FIG. 4A shows an example of a B-scan with an example of GA annotation.
Figure 4B:
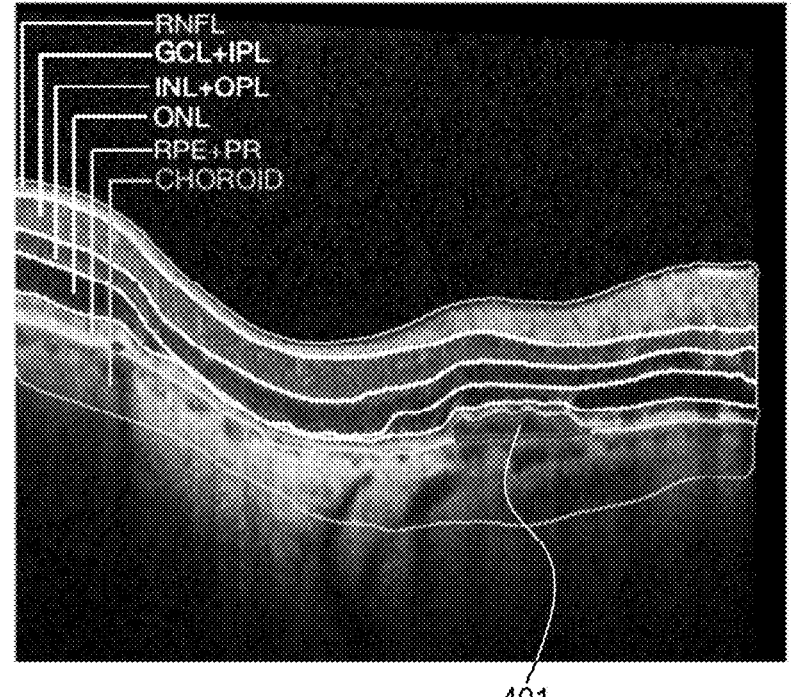
FIG. 4B shows the B-scan of FIG. 4A with segmented layers.

Our data is annotated by an experienced clinician, who drew bounding boxes around atrophic regions in every OCT volume slice (B-scan), example shown in FIG. 4a. Even though we only train on the projection image, annotation is more accurate within B-scans. We then calculate the ground-truth as 2-d en-face atrophy projections. Our dataset consists of 10 patients with multiple OCT acquisition over time. The acquisitions are, however, not necessarily evenly spaced in time.

FIG. 4A shows an example of a B-scan with an example of GA annotation. FIG. 4B shows the B-scan with segmented layers and PED fluid 401.

Figure 6:
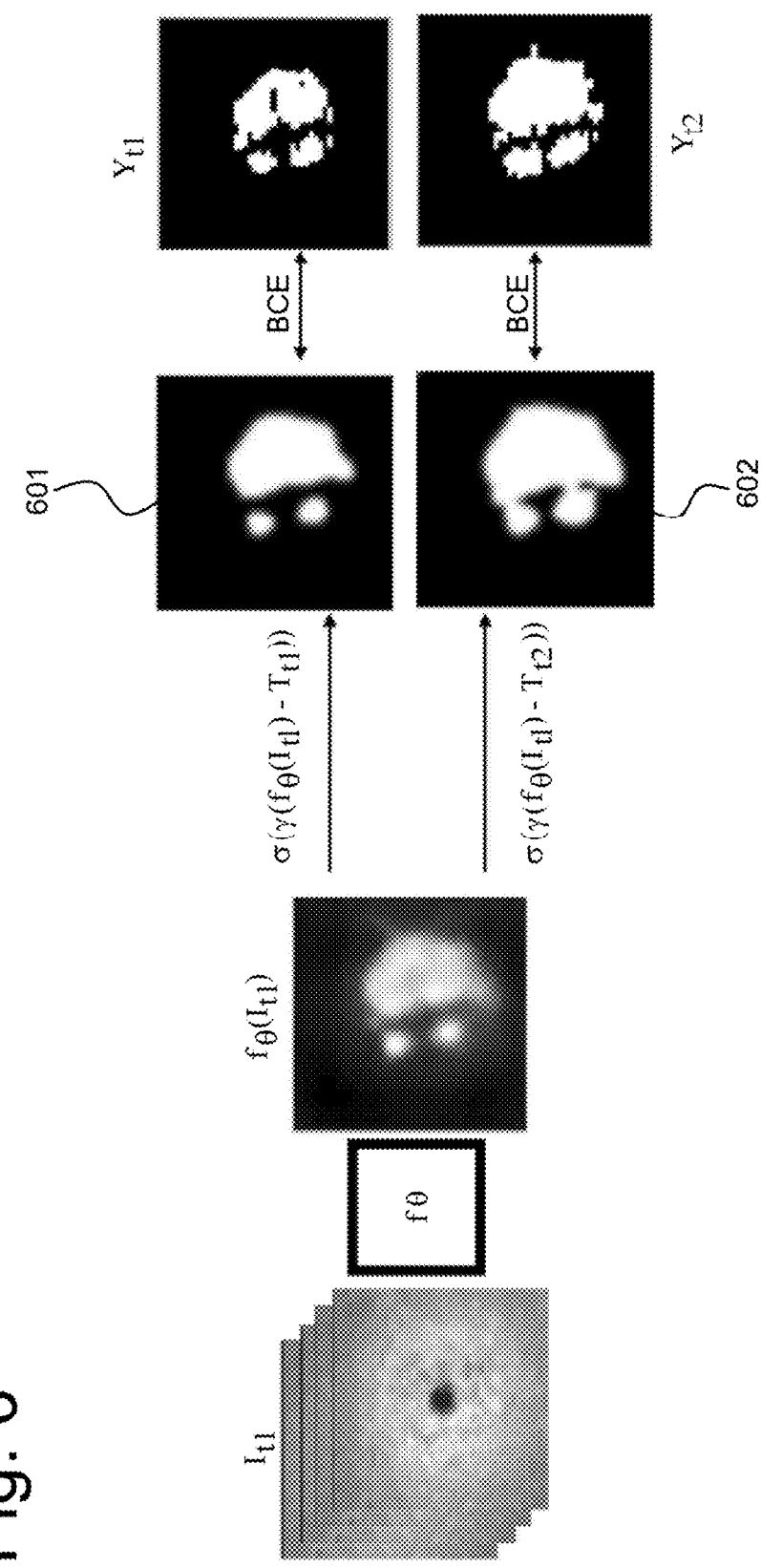
FIG. 6 shows an outline of an example training workflow in accordance with an embodiment of the present disclosure.

FIG. 6 shows an outline of an example training workflow of a method in accordance with an embodiment of the present disclosure. The Figure illustrates the following steps, from left to right: Input images $I_{t_1}$ for a time $t_1$; application of the mapping $f_\theta$; the resulting image $f_\theta(I_{t_1})$. Next, following the upper path: application of function $\sigma(\bar{\gamma}(f_\theta(I_{t_1}) - T_{t_1}))$, and the resulting image 601; binary cross-entropy (BCE) calculation, and the resulting image $Y_{t_1}$. Following the lower path from the image $f_\theta(I_{t_1})$, the diagram of FIG. 6 shows the application of function $\sigma(\bar{\gamma}(f_\theta(I_{t_1})-T_{t_2}))$, and the resulting image 602; binary cross-entropy (BCE) calculation, and the resulting image $Y_{t_2}$.

To be able to find parameters $\theta$ of the Convolutional Neural Network (CNN) $f_\theta$ defined above, we introduce a novel training procedure depicted in FIG. 6. For each patient we extract all possible pairs of acquisitions $P_{a,b}$, for time points $t_a \neq t_b$ and $t_a < t_b$. For each pair $P_{a,b}$ we compute prediction $f_\theta(I_a)$ based on the first thickness map $I_a$, that is from the earlier visit. We then match the prediction twofold: to the ground truth $Y_a$ corresponding to $I_a$ and the future atrophy state $Y_b$ corresponding to $I_b$. Matching is performed by finding two optimal threshold on $G_{t>t_0}$ for $Y_a$ and $Y_b$, respectively, that optimize the Dice Similarity Coefficient, resulting in thresholds $T_a$, $T_b$. The network output is then shifted according to the found thresholds $T_a$, $T_b$, normalized to mean 0.0 and standard deviation 1.0, scaled and finally passed through the sigmoid function. The binary cross-entropy loss corresponding to pair $P_{a,b}$ is then computed as follows:

$$L_{a,b} = \sum_{k\in(a,b)} BCE(Y_k, \sigma(\bar{\gamma}(f_\theta(I_a) - T_k))) \qquad \text{(Equation 1)}$$

where $Y_k$ is the ground truth segmentation of GA at time point k, $\bar{\gamma}$ is normalization followed by scaling and $T_k$ threshold for $f_\theta(I_a)$ yielding the best segmentation with respect to $Y_k$ measured with the Dice Similarity Coefficient. We found that normalizing the output stabilizes training, and scaling it by 100 prior to applying sigmoid increases the range of values to better distinguish time points. The above formulation can be extended to multiple simultaneously trained time points by adding loss terms for each time point.

We leave the thresholds $T_b$ and $T_a$ unbounded in the sense that every time we calculate the thresholds that best approximate the current GA. Each unique threshold represents a level-set and by selecting the optimal one we define the region that best fits the ground truth GA. We chose to let thresholds be unbounded, since absolute GA progression rate is highly patient-dependent in terms of genetic predisposition and lifestyle [3, 5]. Additionally the output of $G_{t>t_0}$ gives an additional insight about the relative speed of progression: large values indicate an immediate future growth, while small value indicates regions affected further in the future.

2.2. Inference

During inference time we use only acquisitions taken at time to $t_0$ obtain predictions $f_\theta(I_{t_0})$, which is then thresholded at decreasing thresholds to obtain a growth profile. Since progression of GA is highly patient-specific we do not predict absolute speed, but rather the relative speed compared to the rest of the retina.

2.3. Implementation Details

The following implementation details are provided as a non-limiting example. We implement a standard encoder/decoder style network with four down-sampling steps and 16, 32, 64, 128 and 256 filters per level. We use the above described loss and optimize it with the Adam optimizer [6] with a learning rate of 0.0001. We scale the original thickness maps to size 150×150. Due to limited training data we perform dynamic data augmentation coherent with natural imaging variations. This includes image rotation (−14.3, +14.3 degrees) and translation (−1%, +1% of image size, in x and y axis). Since the left and the right eye are horizontal mirror images, we also use left/right flipping.

3. Results

3.1. Data and Baselines

We used a dataset of 10 patients, each having from 3 to 5 acquisitions at variable time intervals, resulting in a total of 51 OCT volumes, imaged with a Heidelberg Spectralis OCTs machine. The intervals vary from 5 to 22 months. However, as we will show, thanks to our flexible training procedure, we do not require fixed time intervals. The dataset was manually annotated by an expert on every slice for every time point. Atrophy was selected with a bounding box encompassing the horizontal extent (incomplete RPE and outer retinal atrophy (iRORA) and complete RPE and outer retinal atrophy (cRORA) regions (see FIG. 4a). The ground-truth was obtained by projecting these bounding boxes to 2-d (FIG. 5(j)). To fully leverage the limited number of patients, we perform a leave-one-out cross validation on the patient level, at each fold setting one patient aside for testing. We compare our method to two baselines:

1. Ours: the proposed method (see Section 2)
2. Current Only: the network is trained using only the current thickness image and ground-truth, without access to the future ground-truth during training. It indicates how well current atrophy shape indicates future progression.
3. Zhang et al. [13]: this method jointly predicts current and future atrophy. Contrary to our method it is trained only for specific time intervals (next acquisition). Progressive atrophy is computed using the current atrophy prediction and low-level image features. Current and future atrophy are returned on two separate channels.

3.2. Discussion

Figures 7A, 7B:
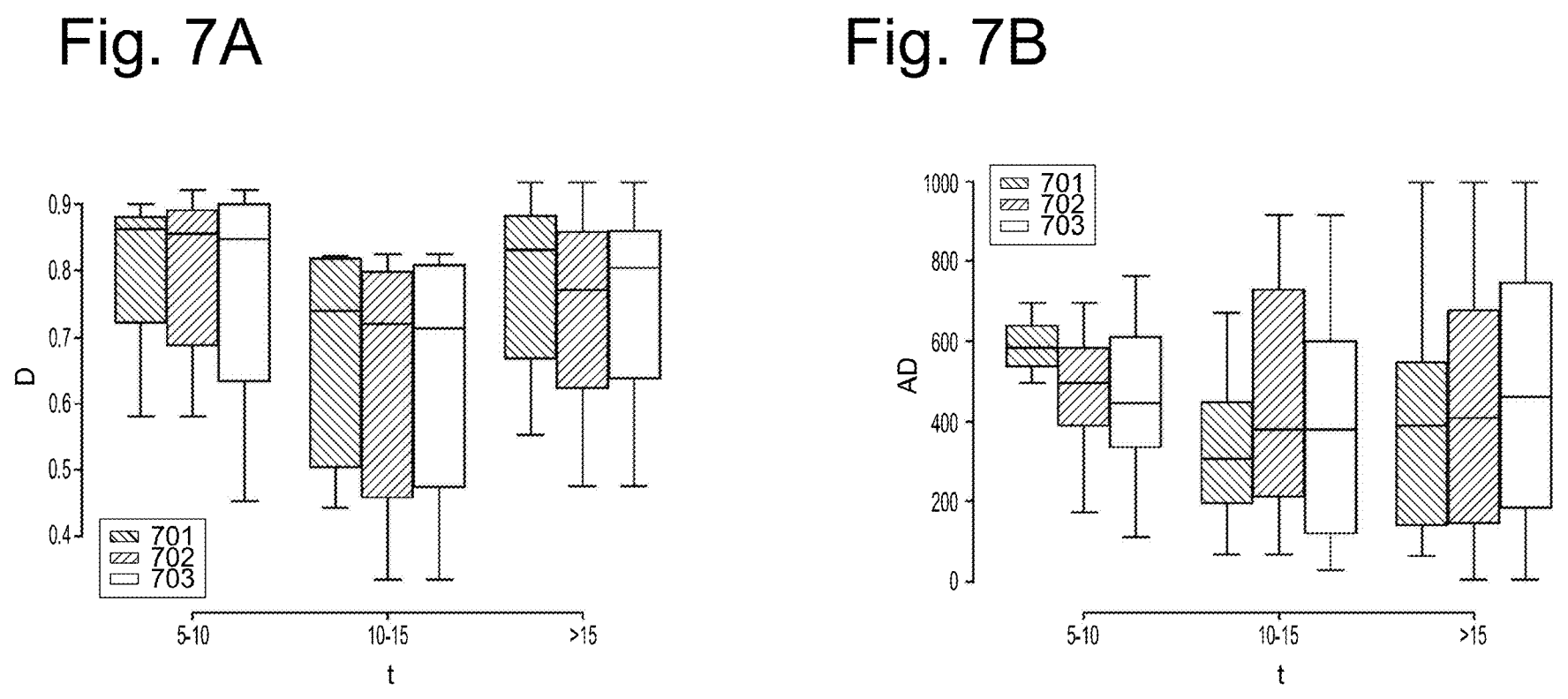

FIG. 7A shows (on the vertical axis "D") Dice scores of the evaluated methods ('Ours' 701, 'Current Only' 702, 'Zhang et al.' 703) for progression prediction versus (on the horizontal axis "t") the time interval in months. FIG. 7B shows (on the vertical axis "AD") Area Difference scores, in pixels, of the evaluated methods for progression prediction versus the time interval in months. The higher Dice Score and lower Area Difference the better.

As can be seen in FIG. 7A, our method outperforms baselines in every time-interval, with the most significant difference in the long-run prediction (>15 months). Current Only and Zhang et al. perform similarly in the short time-span, but the performance decreases with time. This indicates that current atrophy prediction (Current Only) is a good indicator of progression in the short-run even when it is not trained with any future data, as small changes that lead to GA can be already detected at time $t_0$. Zhang et al. outperforms Current Only in longer intervals, but it does not achieve the same performance as Ours.

Figure 8:
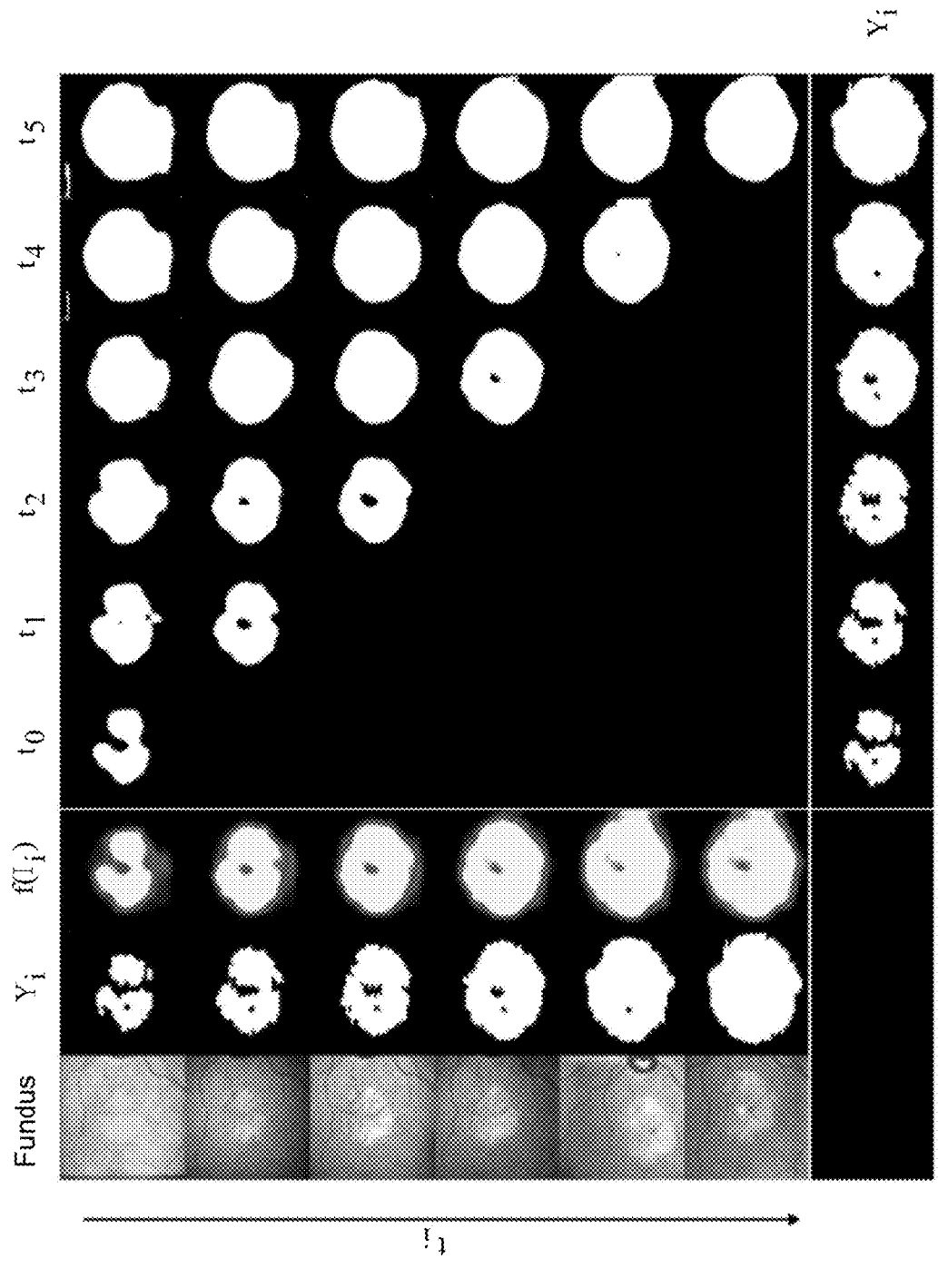
FIG. 8 shows an overview of the results for a single patient.

FIG. 8 shows, by means of example, an overview of the results for a single patient. The first column $I_i$ depicts the (non-aligned) corresponding fundus image for all imaged time points. Corresponding to it in column $Y_i$ is the ground truth segmentation derived from the OCT. The third column $f(I_i)$ shows the predicted level sets based on inputs $I_i$. In the right part of the figure we show the optimal level set for a certain time point.

FIG. 8 depicts the full progression profile in the example of a single patient. The first row shows that our method is able to predict future GA even for long-range intervals. Our level-set formulation ensures that the progression pattern is smooth and continuous, unlike the method of Zhang et al., which optimizes the network to fit discrete atrophy progression. In the shorter period our method achieves lower precision than the two baselines, which is reflected in bigger area difference error for the shortest time intervals (FIG. 7b). This is because it was trained to match progression both in the short and long term. In the end it generalizes better for longer visit times compared to the other methods.

4. Conclusion

In the present disclosure we propose, inter alia, a novel method for learning a continuous GA progression profile prediction. Contrary to previous approaches, we base our method on time points that do not need to be spaced equally in time. We can provide accurate estimations for future atrophic regions beyond the next subsequent time-point. We evaluate our method on a dataset containing patients with non-curated visit intervals, predicting accurate progression profiles beyond the 15 month threshold, and showing promising results towards a real world sparse acquisition scheme.

Some or all aspects of the invention may be suitable for being implemented in the form of software, in particular a computer program product. The computer program product may comprise a computer program stored on a non-transitory computer-readable media. Also, the computer program may be represented by a signal, such as an optic signal or an electro-magnetic signal, carried by a transmission medium such as an optic fiber cable or the air. The computer program may partly or entirely have the form of source code, object code, or pseudo code, suitable for being executed by a computer system. For example, the code may be executable by one or more processors.

The examples and embodiments described herein serve to illustrate rather than limit the invention. The person skilled in the art will be able to design alternative embodiments without departing from the spirit and scope of the present disclosure, as defined by the appended claims and their equivalents. Reference signs placed in parentheses in the claims shall not be interpreted to limit the scope of the claims. Items described as separate entities in the claims or the description may be implemented as a single hardware or software item combining the features of the items described.

REFERENCES

1. Apostolopoulos, S., De Zanet, S., Ciller, C., Wolf, S., Sznitman, R.: Pathological oct retinal layer segmentation using branch residual u-shape networks. In: Medical Image Computing and Computer Assisted Intervention. pp. 294-301 (2017)
2. Arcadu, F., Benmansour, F., Maunz, A., Willis, J., Haskova, Z., Prunotto, M.: Deep learning algorithm predicts diabetic retinopathy progression in individual patients. npj Digital Medicine 92(2) (2019)
3. Boyer, D. S., Schmidt-Erfurth, U., van Lookeren Campagne, M., Henry, E. C., Brittain, C.: The pathopysiology of geographic atrophy secondary to Age-related Macular Degeneration and the complement pathway as a therapeutic target. Retina 37(5) (2017)
4. Engwer, C., Hillen, T., Knappitsch, M., Surulescu, C.: Glioma follow white matter tracts: a multiscale dti-based model. Journal of mathematical biology 71 (09 2014) 5. Fleckenstein, M., Mitchell, P., Freund, K. B., Sadda, S., Holz, F. G., Brittain, C., Henry, E. C., Ferrara, D.: The progression of geographic atrophy secondary to agerelated macular degeneration. Ophthalmology 125(3), 369{390 (2018)

6. Kingma, D. P., Ba, J.: Adam: A method for stochastic optimization. In: International Conference on Learning Representations (2015)
7. Mosayebi, P., Cobzas, D., Murtha, A., Jagersand, M.: Tumor invasion margin on the riemannian space of brain fibers. Medical Image Analysis 16(2), 361-373 (2012)
8. Niu, S., de Sisternes, L., Chen, Q., Leng, T., Rubin, D. L.: Automated geographic atrophy segmentation for SD-OCT images using region-based C-V model via local similarity factor. Biomedical Optics Express 7(2), 581 (2016)
9. Niu, S., de Sisternes, L., Chen, Q., Rubin, D. L., Leng, T.: Fully automated prediction of geographic atrophy growth using quantitative Spectral-Domain Optical Coherence Tomography biomarkers. Ophthalmology 123(8), 1737{1750 (2016)
10. Petersen, J., Jager, P. F., Isensee, F., Kohl, S. A. A., Neuberger, U., Wick, W., Debus, J., Heiland, S., Bendszus, M., Kickingereder, P., Maier-Hein, K. H.: Deep Probabilistic Modeling of Glioma Growth (2019)
11. Ronneberger, O., Fischer, P., Brox, T.: U-net: Convolutional networks for biomedical image segmentation. In: Medical Image Computing and Computer-Assisted Intervention. vol. 9351, pp. 234{241 (2015)
12. Sadda, S. R., Guymer, R., Holz, F. G., Schmitz-Valckenberg, S., Curcio, C. A., Bird, A. C., Blodi, B. A., Bottoni, F., Chakravarthy, U., Chew, E. Y., Csaky, K., Danis, R. P., Fleckenstein, M., Freund, K. B., Grunwald, J., Hoyng, C. B., Jaffe, G. J., Liakopoulos, S., Monés, J. M., Pauleikhoff, D., Rosenfeld, P. J., Sarraf, D., Spaide, R. F., Tadayoni, R., Tufail, A., Wolf, S., Staurenghi, G.: Consensus definition for atrophy associated with Age-Related Macular Degeneration on OCT: classification of atrophy report 3. Ophthalmology 125(4), 537-548 (2018)
13. Zhang, Y., Ji, Z., Niu, S., Leng, T., Rubin, D. L., Chen, Q.: A multi-scale deep convolutional neural network for joint segmentation and prediction of geographic atrophy in SD-OCT images. 2019 IEEE 16th International Symposium on Biomedical Imaging (ISBI 2019) (Isbi), 565-568 (2019).

The invention claimed is:

1. A method of predicting a progression of a condition, the method comprising:

obtaining measurement data relating to at least one measurement on a subject up to a particular time point, wherein the data is generated based on an output of a sensor configured to perform the at least one measurement in respect of the subject, wherein the measurement data comprises at least one N-dimensional input dataset of pixels or voxels associated with the subject, generated by an imaging device, wherein Nis a positive integer value, wherein the N-dimensional input dataset is an at least two-dimensional image dataset associated with the subject;

generating, for each of a plurality of the pixels or voxels within the N-dimensional input dataset, at least one parameter of a parameterized time-dependent function, using a trained model and based on the measurement data, wherein the parameterized time-dependent function is dependent on a continuous time value, and wherein the parameterized time-dependent function is indicative of a predicted progression of a condition of the subject over time after the particular time point, for each of the plurality of the pixels or voxels separately.

2. The method of claim 1, further comprising evaluating the parameterized time-dependent function using the at least one parameter, for at least one time point after the particular time point.

3. A method of training a model to predict a progression of a condition, the method comprising obtaining training data comprising measurement data relating to at least one measurement on at least one subject, wherein the measurement data is based on an output of a sensor configured to perform the at least one measurement in respect of the subject, wherein the measurement data comprises at least one N-dimensional input dataset of pixels or voxels associated with the subject, generated by an imaging device, wherein N is a positive integer value, wherein the N-dimensional input dataset is an at least two-dimensional image dataset associated with the subject, the training data further comprising, for each subject, at least one time point associated with the subject, and information indicative of a condition of the subject at the at least one time point;

generating, for each of a plurality of the pixels or voxels within the N-dimensional input dataset, at least one parameter of a parameterized time-dependent function, wherein the parameterized function is dependent on a continuous time value, using a model and based on the measurement data of a certain subject of the at least one subject, wherein the parameterized time-dependent function is indicative of a predicted progression of the condition of the certain subject over time, for each of the plurality of the pixels or voxels separately;

evaluating the parameterized time-dependent function using the at least one parameter, for the at least one time point associated with the certain subject, to obtain a predicted condition of the subject at the at least one time point;

comparing the predicted condition of the certain subject at the at least one time point associated with the certain subject to the information in the training data indicative of the condition of the certain subject at the at least one time point associated with the certain subject, to obtain a comparison result; and updating the model based on the comparison result.

4. The method of claim 3, wherein at least one first subject of the at least one subject has a first set of at least one time point associated therewith, at least one second subject of the at least one subject has a second set of at least one time point associated therewith, and at least one time point in the first set is different from each time point in the second set.

5. The method of claim 3, wherein the at least one parameter is indicative of a time point when the condition will change or a speed at which the condition will change.

6. The method of claim 5, wherein evaluating the parameterized time-dependent function comprises applying a threshold to the parameter that is generated using the model, wherein the threshold depends on the time point at which the parameterized time-dependent function is evaluated.

7. The method of claim 3, wherein the at least one parameter comprises at least one coefficient of a term of the parameterized time-dependent function.

8. The method of claim 7, wherein the parameterized time-dependent function comprises a Fourier series or a Taylor series.

9. The method of claim 3, wherein the model comprises a convolutional neural network.

10. An apparatus for training a model to predict a progression of a condition, the apparatus comprising an input configured to receive training data comprising measurement data relating to at least one measurement on at least one subject, wherein the measurement data is based on an output of a sensor configured to perform the at least one measurement in respect of the subject, wherein the measurement data comprises at least one N-dimensional input dataset of pixels or voxels associated with the subject, generated by an imaging device, wherein N is a positive integer value, wherein the N-dimensional input dataset is an at least two-dimensional image dataset associated with the subject, the training data further comprising, for each subject, at least one time point associated with the subject, and information indicative of a condition of the subject at the at least one time point;

a storage media for storing a model; and a processor system configured to cause the apparatus to:

generate, for each of a plurality of the pixels or voxels within the N-dimensional input dataset, at least one parameter of a parameterized time-dependent function, wherein the parameterized time-dependent function is dependent on a continuous time value, using the model and based on the measurement data of a certain subject of the at least one subject, wherein the parameterized time-dependent function is indicative of a predicted progression of the condition of the certain subject over time, for each of the plurality of the pixels or voxels separately, evaluate the parameterized time-dependent function using the at least one parameter, for the at least one time point associated with the certain subject, to obtain a predicted condition of the subject at the at least one time point, compare the predicted condition of the certain subject at the at least one time point associated with the certain subject to the information in the training data indicative of the condition of the certain subject at the at least one time point associated with the certain subject, to obtain a comparison result, and update the model based on the comparison result.

11. The method of claim 1, wherein the at least one parameter is indicative of a time point when the condition will change or a speed at which the condition will change.

12. The method of claim 11, wherein evaluating the parameterized time-dependent function comprises applying a threshold to the parameter that is generated using the model, wherein the threshold depends on the time point at which the parameterized time-dependent function is evaluated.

13. The method of claim 1, wherein the at least one parameter comprises at least one coefficient of a term of the parameterized time-dependent function.

14. The method of claim 13, wherein the parameterized time-dependent function comprises a Fourier series or a Taylor series.

15. The method of claim 1, wherein the model comprises a convolutional neural network.

* * * * *